United States Patent [19]

Vcelka

[11] 4,364,383

[45] Dec. 21, 1982

[54] I.V. FLASHBACK INDICATION

[76] Inventor: John L. Vcelka, 905 Wilson Ct., Zion, Ill. 60099

[21] Appl. No.: 181,299

[22] Filed: Aug. 25, 1980

[51] Int. Cl.³ .............................................. A61M 5/14
[52] U.S. Cl. ............................................... 128/214 R
[58] Field of Search ........... 128/214 R, 214 C, 214 G, 128/214.2

[56] References Cited

U.S. PATENT DOCUMENTS

| | | | |
|---|---|---|---|
| 2,702,036 | 2/1955 | Bent | 128/214 C |
| 2,758,598 | 8/1956 | Cutter | 128/214 C |
| 2,868,200 | 1/1959 | Gewecke | 128/214 G |
| 3,429,311 | 2/1969 | Wickett | 128/214G |
| 3,674,404 | 7/1972 | Burlis et al. | 425/326 |

Primary Examiner—Dalton L. Truluck

[57] ABSTRACT

A flashback indicator which is integrally formed in a parenteral solution or blood set to serve as a patency check device. A length of clear plastic tubing having an enlarged portion is integrally connected in a parenteral fluid or blood set in such a manner that a patency check can be made without fear of the indicator becoming disconnected from the set during the supplementary administration of a drug such as by means of a hypodermic syringe. In a preferred manner, the flashback indicator is formed from bubble-like tubing wherein the wall thickness of the enlarged portion of the bubble is at least as large as that of the tubing in the set having a smaller and constant diameter.

9 Claims, 4 Drawing Figures

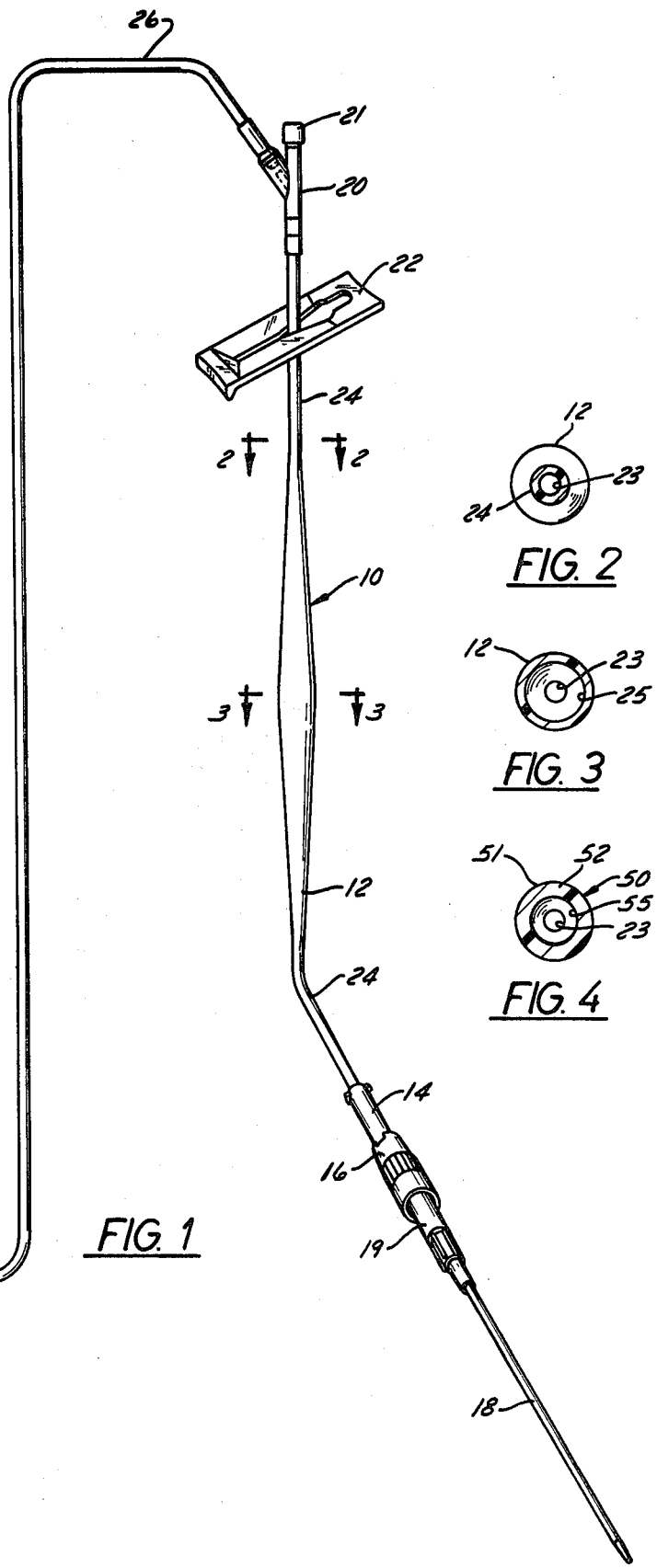
FIG. 1
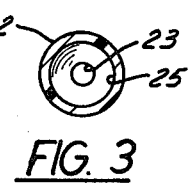
FIG. 2
FIG. 3
FIG. 4

I.V. FLASHBACK INDICATION

BACKGROUND OF THE INVENTION

This invention relates to a flashback or patency check device to indicate proper venipuncture in conjunction with a blood or parenteral administration set. More particularly, this invention relates to a flashback component which is formed as an intregral unit and will not become detached from the set during normal usage.

Flashback indicators of the type concerned with in this invention are described in the Gewecke U.S. Pat. No. 2,868,200. As explained therein, one of the functions of a flashback indicator is to show that the hypodermic needle or catheter through which the fluid enters the body has indeed punctured a vein. The problem with the unit described in the Gewecke patent is that it is difficult to obtain a seal between the tubing which is typically polyvinyl choride and the flashback indicator which is typically latex so that it can withstand the pressures exerted in the set when a hypodermic syringe is utilized to administer additional medication. When these materials are employed, the only bond is friction. In many instances where such a syringe has been employed, sets utilizing these components have been known to break apart or leak at the junction of the tubing and the flashback indicator. Where the flashback indicators have been blown off the sets, much distress has been caused to the patient as well as causing much concern to the administrator of the I.V. fluids as the patient is in many instances already under an emergency condition.

U.S. Pat. No. 3,674,404 issued to Burlis, et al. describes bubble tubing which is extruded with various external and internal diameters as well as wall thicknesses. The tubing is indicated for use in various types of catheters, drainage and aspiration tubes as well as tubing having tapered end portions for interconnecting various biomedical devices.

Nowhere in the prior art is there provided a flashback or patency check device which can be formed as an integral part of a parenteral or blood I.V. administration set so that entry into a vein is immediately indicated yet additional medication can be administered quickly and under rapid and relatively high pressure conditions without the flashback indicator being disconnected from the set.

It is an advantage of the present invention to provide a flashback or patency check device which can be formed integrally with an I.V. administration set and which will not become detached during normal usage. Other advantages are a flashback indicator which is economical to manufacture and assemble; can be constructed in various configurations and sizes to fit the various capacities of I.V. administration sets; can be formed as a portion of the flexible tubing in an I.V. administration set thereby reducing the cost thereof.

SUMMARY OF THE INVENTION

The foregoing advantages are accomplished and the shortcomings of the prior art are overcome by the present flashback or patency check device which is integrally formed in a length of flexible tubing which length of tubing is transparent and finger squeezable. The tubing is composed of a resinous plastic material compatible with parenteral solutions and the flashback is formed by an enlarged portion in the passageway of the tubing. The tubing has a wall thickness in the enlarged portion at least as thick as in the tubing immediately adjacent the enlarged portion which has a smaller and constant diameter. First and second component members which are of the type normally utilized in a parenteral solution administration set are secured to opposite ends of the tubing forming the flashback indicator. The tubing is secured to the components in such a manner that it will remain intact with the components even when the tubing is subjected to internal pressures normally associated with hypodermic syringes and in excess of 29 PSIG. In a preferred manner, the flashback indicator will have a wall thickness in the enlarged portion greater than that of the tubing normally supplied with an I.V. administration set. Also preferably, the enlarged portion will be of a generally elongated diamond shape and will be composed of a flexible thermoplastic material. The passageway in the enlarged portion will preferably be in the range of about 0.200 inches to about 0.400 inches in diameter.

DESCRIPTION OF THE DRAWING

A better understanding of the patency check device will be accomplished by reference to the drawing wherein:

FIG. 1 is a view in side elevation of a parenteral administration set including the flashback or patency check device of this invention.

FIG. 2 is a view in horizontal section taken through line 2—2 of FIG. 1.

FIG. 3 is a view in horizontal section taken through line 3—3 of FIG. 1.

FIG. 4 is a view similar to FIG. 3 except showing an alternative embodiment.

DESCRIPTION OF ONE EMBODIMENT

Proceeding to a detailed description of the present invention, the patency check device 10 is shown in FIG. 1 in conjunction with the usual parenteral administration set. Such a set will include the usual components such as a hypodermic needle 18 interconnected to flashback indicator 10 by means of hub 19 being retained on needle adapter 14 by means of rotatable collar 16. A length of tubing 24 of the usual diameter and passageway and normally supplied with an I.V. set interconnects the flashback indicator 10 with the needle adapter 14. At the opposite end, a similar length of tubing 24 interconnects the flashback indicator with a Y reseal unit 20 from which extends a length of tubing 26 ultimately connected with a second Y reseal site 32. This Y reseal site is interconnected with drip chamber 36 by means of a short length of tubing 34. Communication is made to the inside of container 40 by means of piercing pin 38. In the instance where container 40 is a rigid container, the piercing pin 38 will be vented to outside atmosphere in the usual manner. A flow control clamp 30 and an on-off slide clamp 22 are also provided.

It will be noted that flashback indicator 10 is in effect formed as an integral portion of a length of tubing and coextensive with tubing lengths 24. It is generally of an elongated diamond shape as illustrated by the configuration of tubing 12 forming a part thereof. FIG. 2 illustrates a wall thickness of tubing 24 with the usual passageway 23 therein. FIG. 3 is shown for purposes of comparing the wall thickness and in this instance the wall thickness of the patency check portion 10 as formed by the enlarged diameter portion of tubing 12 will have the same wall thickness as for tubing 24. It will be noted in this instance that the passageway 25 as formed by the diameter of wall portion 12 will be substantially larger than that of passageway 23 in length of tubing 24 which is immediately adjacent to the patency check portion.

FIG. 4 represents an alternative embodiment 50 of the patency check unit. It, as is true of unit 10, will be formed integrally in a length of flexible tubing and will be coextensive at each end with length of tubing normally employed in parenteral administration sets. In this instance, the thickness of the wall 52 of tubing 51 at the widest diameter of the flashback indicator will be larger than the wall thickness 24. Enlarged passageway 55 will be larger than passageway 23.

Operation

A better understanding of the advantages of the flashback indicators 10 and 50 will be had by a description of their assembly and operation. Whether the flashback indicator 10 or 50 is utilized, a method of fabricating the tubing can be in utilizing the extruder apparatus and process indicated in the previously referred to U.S. Pat. No. 3,674,404. A length of tubing with the enlarged portion such as shown at 12 will be cut into suitable lengths and secured to I.V. components such as needle adapter 14 and Y reseal 20 by means of solvent bonding, heat sealing or RF welding. The flashback indicator 10 and 50 will be supplied as part of the I.V. administration set illustrated in FIG. 1 except that it will not be interconnected with solution container 40. At the time of administration, the set will be interconnected with container 40 by means of piercing pin 38 and the flashback indicators 10 and 50 will be employed in the usual manner. This means that clamp 22 will be in a closed position when needle 18 is inserted into a vein. If proper venipuncture is made, blood will flash back into flashback unit 10 or 50 which is facilitated by the enlarged section of tubing 12 and 52. If there is any doubt whether proper venipuncture has been made, flashback unit 50 can be squeezed with the fingers to effect an aspiration of blood for venipuncture verification. During the administration of solution from container 40, which will be effected by moving clamp 22 to the open position and adjusting the flow with roller clamp 30, it may become necessary to inject secondary medication. This will be effected by means of a hypodermic syringe and needle which will be pierced through reseal cap 21. It will be appreciated that when this is effected by means of a hypodermic syringe, pressures in the range of at least 29 PSIG will be experienced. Where a flashback indicator such as previously referred to in the Gewecke patent was utilized, the flashback indicator could literally be blown away from the tubing because of the problems of attempting to seal I.V. plastic tubing to a rubber-like flashback indicator. This problem is obviated in the present flashback indicators 10 and 50 due to the fact that they are integrally molded as a portion of tubing such as illustrated in the numerals 12 and 24. There is no problem with the flashback indicator separating from tubing 24 and the connections made at the opposing ends of tubing 24 can be effectively made as plastic tubing 24 is being sealed to plastic components 20 and 14.

In FIG. 4, a flashback indicator generally of the same type as shown at 10 is utilized except that the wall thickness 52 is larger than the wall thickness for tubing 12. This is for the purpose of keeping the bubble from expanding when injections are made into latex injection site 21.

An important aspect of the invention is that not only are the flashback indicators formed as an integral portion of a length of tubing, but that the wall thickness of the widest diameter portion of the indicator such as illustrated in FIG. 3, could be of a dimension at least as large and as thick as in the regular length of tubing such as shown in 24. This, as previously explained, is for the purpose of preventing expansion during injection of additive materials. Further, the length of tubing such as shown at 12 and 51 should be transparent so that the blood flowing into it is readily discernible and should be finger squeezable for aspiration purposes. It has been found that tubing composed of polyvinyl chloride and having an outside diameter of 0.170 in. and an inside diameter of 0.120 in. at its smallest diameter with a maximum diameter of 0.380 in. and an inside diameter of 0.300 in. at its maximum point has been found to work well. Preferably, the diameter for the enlarged passageway 25 will be 0.250 in. and for the normal passageway 23 0.120 in. However, these dimensions are not critical and can range from 0.60 in. to 0.180 in. for the passageway of the tubing of a diameter as indicated at 24 to 0.200 in. to 0.400 in. at the enlarged portion indicated by 12 and 51 in. FIGS. 3 and 4.

In the previous description, tubing composed of polyvinyl chloride has been indicated as being preferred. However, any tubing which is transparent and semiflexible can be employed such as polyurethane, silicone polyethylene or polypropylene. The components such as the reseal unit body 20 and the needle adapter 14 are preferably formed of a rigid polyvinylchloride material but can be of any rigid resinous material which is easily and securely solvent bonded to the flexible tubing. However, as will be recognized, other bonding or sealing methods such as heat sealing or RF welding can be employed as dictated by the composition of the components and the tubing.

In the previous description, the term "parenteral administration sets" has been employed as well as a "blood administration set." It should be understood that for purposes of the invention these terms are interchangeable as the flashback indicator can be as readily utilized in conjunction with a parenteral solution such as saline or an amino acid solution as well as with a blood set.

It will thus be seen that through the present invention there is now provided a flashback indicator which can be integrally molded in a length of tubing and secured to an I.V., parenteral or blood administration set in such a manner that it will not become detached when secondary administrations are made such as with a hypodermic syringe. The flashback indicator can be easily molded and secured to the set at a minimum of cost yet it is readily utilized in the manner previously employed for flashback or patency check units.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. In an I.V. administration set including first and second component members of the type normally utilized in a parenteral solution administration set with flexible tubing secured to said components and one of said components including means for attachment to a hypodermic needle, said flexible tubing composed of a resinous plastic material compatible with parenteral solutions and secured to said first and second components in a manner such that the component members will remain integrally attached to said tubing even when said tubing is subjected to internal pressures normally associated with hypodermic syringes, the improvement comprising a flashback indicator of one-piece construction defined by an enlarged portion in the passageway of the tubing with said tubing having a wall thickness in said enlarged portion greater than the wall thickness of the tubing immediately adjacent said enlarged portion.

2. The flashback indicator as defined in claim 1 wherein said enlarged portion is of a generally elongated diamond shape.

3. The flashback indicator as defined in claim 1 wherein one of said components is a hypodermic needle adapter.

4. The flashback indicator as defined in claim 1 wherein said tubing is composed of a polyvinyl chloride plastic material.

5. The flashback indicator as defined in claim 1 wherein one of said components includes an injection site for a hypodermic syringe.

6. The flashback indicator as defined in claim 1 wherein said components are integrally secured to said tubing by means of solvent bonding.

7. The flashback indicator as defined in claim 1 wherein said components are composed of a silicone, polyurethane, polyethylene or polypropylene plastic material.

8. The flashback indicator as defined in claim 1 wherein the diameter of said passageway in said enlarged portion is in the range of about 0.200 in. to about 0.400 in.

9. The flashback indicator as defined in claim 4 wherein said diameter of said passageway in said enlarged portion is 0.250 in.

* * * * *

UNITED STATES PATENT AND TRADEMARK OFFICE
CERTIFICATE OF CORRECTION

PATENT NO. : 4,364,383
DATED : December 21, 1982
INVENTOR(S) : John L. Vcelka

It is certified that error appears in the above—identified patent and that said Letters Patent is hereby corrected as shown below:

Title should be corrected to read:

I.V. FLASHBACK INDICATOR

Assignee should be shown as:

Abbott Laboratories
    North Chicago, Ill.

Signed and Sealed this

Twelfth Day of June 1984

[SEAL]

*Attest:*

GERALD J. MOSSINGHOFF

*Attesting Officer*     *Commissioner of Patents and Trademarks*